US00PP17777P2

(12) United States Plant Patent
Roberson

(10) Patent No.: US PP17,777 P2
(45) Date of Patent: Jun. 5, 2007

(54) ***LANTANA* PLANT NAMED 'ROBPATGOL'**

(50) Latin Name: *Lantana camara*
Varietal Denomination: Robpatgol

(76) Inventor: Robert J. Roberson, P.O. Box 210, Grain Valley, MO (US) 64029

( * ) Notice: Subject to any disclaimer, the term of this patent is extended or adjusted under 35 U.S.C. 154(b) by 32 days.

(21) Appl. No.: 11/185,459

(22) Filed: Jul. 20, 2005

(51) Int. Cl.
*A01H 5/00* (2006.01)

(52) U.S. Cl. ..... Plt./227

(58) Field of Classification Search ..... Plt./227
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Lantana* plant named 'Robpatgol', characterized by its upright and outwardly spreading plant habit; uniformly mounded plant form; semi-compact growth habit; freely branching habit; short internodes; dense and bushy habit; freely and continuously flowering habit; and flowers that are bright golden yellow in color.

2 Drawing Sheets

Botanical designation: *Lantana camara.*
Cultivar denomination: 'Robpatgol'.

BACKGROUND OF THE INVENTION

The present Invention relates to a new and distinct cultivar of *Lantana* plant, botanically known as *Lantana camara,* and hereinafter referred to by the cultivar name Robpatgol.

The new *Lantana* is a product of a planned breeding program conducted by the Inventor in Grain Valley, Mo. The objective of the breeding program is to create new semi-compact and freely-flowering *Lantanas* with attractive flower coloration.

The new *Lantana* originated from a cross-pollination made by the Inventor in August, 2001 of a proprietary *Lantana* seedling selection identified as code number 99-CRM-TC1, not patented, as the female, or seed, parent with the *Lantana* cultivar Golden Plume, not patented, as the male, or pollen, parent. The new *Lantana* was selected as a single plant from the resulting progeny of the cross-pollination by the Inventor in a controlled environment in Grain Valley, Mo., on the basis of its semi-compact growth habit and attractive flower coloration.

Asexual reproduction of the new cultivar by terminal cuttings in a controlled environment in Grain Valley, Mo., since September, 2002, has shown that the unique features of this new *Lantana* are stable and reproduced true to type in successive generations.

SUMMARY OF THE INVENTION

Plants of the cultivar Robpatgol have not been observed under all possible environmental conditions. The phenotype may vary somewhat with variations in environment and culture such as temperature and light intensity, however, any variance in genotype.

The following traits have been repeatedly observed and are determined to be the unique characteristics of 'Robpatgol'. These characteristics in combination distinguish 'Robpatgol' as a new and distinct *Lantana* cultivar:

1. Upright and outwardly spreading plant habit; uniformly mounded plant form.
2. Semi-compact growth habit.
3. Freely branching habit and short internodes, dense and bushy habit.
4. Freely and continuously flowering habit.
5. Flowers that are bright golden yellow in color.

Plants of the new *Lantana* can be compared to plants of the parents. In side-by-side comparisons conducted in Grain Valley, Mo., plants of the new *Lantana* differed from plants of the female parent selection in the following characteristics:

1. Plants of the new *Lantana* were stronger and faster growing than plants of the female parent selection.
2. Plants of the new *Lantana* were larger than plants of the female parent selection.
3. Plants of the new *Lantana* and the female parent selection differed in flower color as plants of the female parent selection had creamy white-colored flowers.

In side-by-side comparisons conducted in Grain Valley, Mo., plants of the new *Lantana* differed from plants of the male parent, the cultivar Golden Plume, in the following characteristics:

1. Plants of the new *Lantana* were more compact than plants of the cultivar Golden Plume.
2. Plants of the new *Lantana* were more freely branching, had shorter internodes and were more dense than plants of the cultivar Golden Plume.
3. Plants of the new *Lantana* had darker green-colored foliage than plants of the cultivar Golden Plume.
4. Plants of the new *Lantana* were more freely flowering than plants of the cultivar Golden Plume.
5. Plants of the new *Lantana* had more golden-colored flowers than plants of the cultivar Golden Plume.

Plants of the new *Lantana* can also be compared to plants of the *Lantana* cultivar Robpatsun, disclosed in U.S. Plant Pat. No. 10,885. In side-by-side comparisons conducted in Grain Valley, Mo., plants of the new *Lantana* differed from plants of the cultivar Robpatsun in the following characteristics:

1. Plants of the new *Lantana* were more upright than and not as cascading as plants of the cultivar Robpatsun.
2. Plants of the new *Lantana* had darker green-colored foliage than plants of the cultivar Robpatsun.
3. Plants of the new *Lantana* had more intense golden yellow-colored flowers than plants of the cultivar Robpatsun.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Lantana*. Plants used for the photographs were grown in an outdoor nursery in Grain Valley, Mo. for about three months.

The photograph on the first sheet comprises a side perspective view of a typical flowering plant of 'Robpatgol' grown in the landscape for about three months.

The photograph on the second sheet comprises a close-up view of typical inflorescences and leaves of 'Robpatgol'.

DETAILED BOTANICAL DESCRIPTION

In the following description, color references are made to The Royal Horticultural Society Colour Chart, 1995 Edition, except where general terms of ordinary dictionary significance are used. Plants used for the description were planted in containers after rooting and grown for about 3 months during the spring in an outdoor nursery in Tolar, Tex. During the production of the plants in the greenhouse, temperatures ranged from about 18° C. to about 35° C.

Botanical classification: *Lantana camara* cultivar Robpatgol.

Parentage:

*Female, or seed, parent.*—Proprietary *Lantana camara* seedling selection identified as code number 99-CRM-TC1, not patented.

*Male, or pollen, parent.*—*Lantana camara* cultivar Golden Plume, not patented.

Propagation:

*Type cutting.*—Terminal cuttings.

*Time to initiate roots, summer.*—About 14 days at 27° C.

*Time to initiate roots, winter.*—About 16 days at 27° C.

*Time to develop roots, summer.*—About 28 days at 24° C.

*Time to develop roots, winter.*—About 33 days at 24° C.

*Root description.*—Fine, fibrous; initially glaucous white in color then becoming closer to 161D with development.

*Rooting habit.*—Freely branching.

Plant description:

*Form.*—Flowering subshrub; upright and outwardly spreading plant habit; uniformly mounded plant form; compact growth habit. Freely branching; two lateral branches potentially forming at every node; pinching enhances lateral branch development.

*Plant height.*—About 26 cm.

*Plant diameter.*—About 57 cm.

*Lateral branches.*—Length: About 23.5 cm. Diameter: About 4 mm. Internode length: About 2.4 cm. Strength: Strong, but flexible. Texture: Rough, pubescent. Color: Young: Close to 144A. Woody: Close to 199A.

*Foliage description.*—Arrangement: Opposite; simple. Length: About 9 cm. Width: About 5.5 cm. Shape: Ovate. Apex: Acute. Base: Obtuse with truncate tendencies. Margin: Crenate to serrate. Texture, upper and lower surfaces: Leathery, rough, coarse; pubescent. Luster: Upper surface: Slightly glossy. Lower surface: Dull. Venation pattern: Pinnate, arcuate. Color: Developing and fully expanded foliage, upper surface: Darker green than 147A. Developing and fully expanded foliage, lower surface: Close to 147B. Venation, upper surface: Close to 144A. Venation, lower surface: Close to 144B. Petiole length: About 2.6 cm. Petiole diameter: About 3 mm. Petiole texture, both surfaces: Slightly pubescent. Petiole color, upper surface: Close to 144A. Petiole color, lower surface: Close to 144B.

Flower description:

*Flower type and habit.*—Small salverform flowers arranged in axillary umbels; flowers face mostly upward or outward. Flowers self-cleaning. Very freely flowering with potentially two inflorescences per node; typically about 40 flowers per umbel.

*Natural flowering season.*—Spring until frost in the autumn; flowering continuous and consistent.

*Flower longevity on the plant. About one week.*

*Fragrance.*—Faint, pleasant.

*Inflorescence diameter.*—About 5.2 cm.

*Inflorescence height.*—About 3.1 cm.

*Flowers.*—Appearance: Flared trumpet, corolla fused, four-parted; flowers roughly rectangular in shape. Diameter: About 1.5 cm by 1.3 cm. Corolla tube length: About 1.25 cm.

*Flower buds (before showing color).*—Length: About 9 mm. Diameter: About 7 mm. Shape: Roughly ovoid. Color: Close to 144A.

*Corolla.*—Arrangement/appearance: Single whorl of four petals, fused into flared trumpet. Petal length from throat: Upper and lower petals: About 8 mm. Lateral petals: About 6 mm. Petal width: Upper and lower petals: About 9 mm. Lateral petals: About 5 mm. Petal shape: Spatulate to somewhat orbicular. Petal apex: Rounded. Petal margin: Entire. Petal lobe texture, upper and lower surfaces: Smooth, velvety. Corolla throat and tube texture: Pubescent. Color: Petal lobes, when opening, upper surface: Close to 12A. Petal lobes, when opening, lower surface: Close to 12B. Petal lobes, fully opened, upper surface: Close to 9A. Petal lobes, fully opened, lower surface: Close to 9B to 9C. Throat: Close to 9A and 12A. Tube: Close to 9C.

*Calyx.*—Quantity: One sepal per flower. Length: About 7 mm. Width: About 2 mm. Shape: Lanceolate. Apex: Acute. Base: Truncate. Texture, upper and lower surface: Pubescent. Color, upper and lower surfaces: Close to 144A.

*Peduncles.*—Length: About 3.7 cm. Diameter: About 1.5 mm. Angle: About 45° from the stem. Strength: Flexible, but strong. Texture: Pubescent. Color: Close to 144A.

*Pedicels.*—Not observed, flowers not stalked.

*Reproductive organs.*—Stamens: Quantity/arrangement: Four per flower, adnate to floral tube. Anther shape: Oblong. Anther length: Less than 1 mm. Anther color: Close to 9A. Pollen amount: None observed. Pistils: Quantity: One per flower. Pistil length: About 2 mm. Stigma shape: Rounded. Stigma color: Close to 144B to 144C. Ovary color: Close to 144A.

*Fruit.*—Fruit development has not been observed.

Disease/pest resistance: Plants of the new *Lantana* grown in the garden have not been noted to be resistant to pathogens and pests common to *Lantana*.

Weather tolerance: Plants of the new *Lantana* have been observed to be very tolerant to rain and wind.

Temperature tolerance: Plants of the new *Lantana* have been observed to be tolerant to temperatures ranging from 0° C. to 38° C.

It is claimed:

1. A new and distinct cultivar of *Lantana* plant named 'Robpatgol', as illustrated and described.

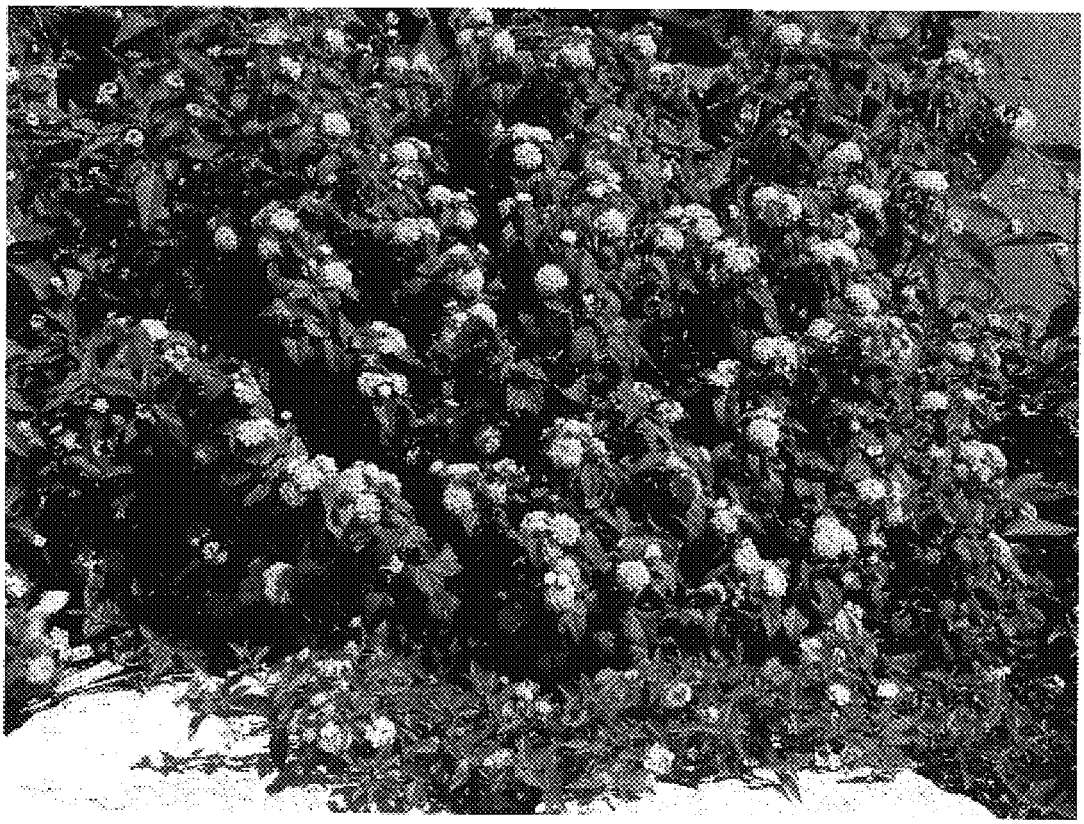

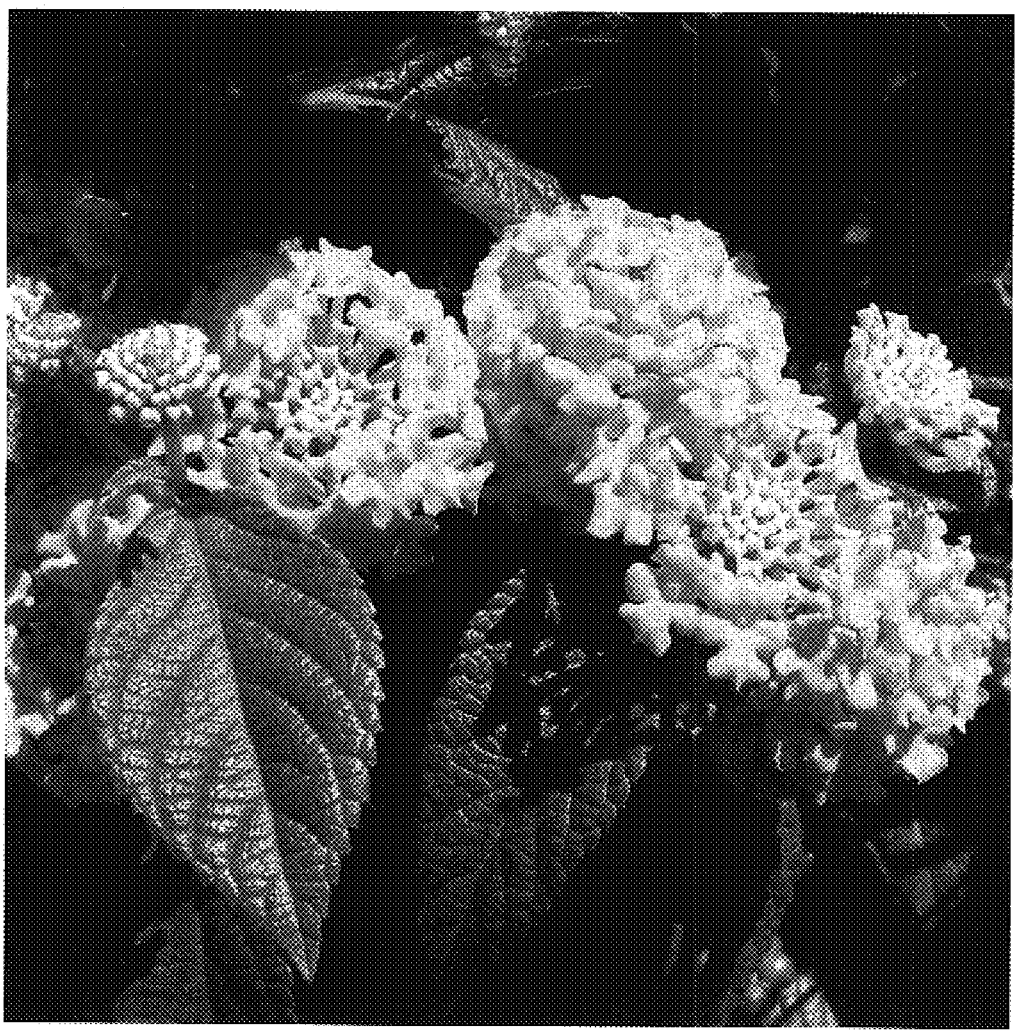

* * * * *